United States Patent [19]
Laing et al.

[11] Patent Number: 6,059,965
[45] Date of Patent: May 9, 2000

[54] PROCESS AND DEVICE TO STERILIZE A STREAM OF WATER

[76] Inventors: Karsten Andreas Laing; Johannes Nikolaus Laing, both of 1253 La Jolla Rancho Rd., La Jolla, Calif. 92037

[21] Appl. No.: 09/024,653

[22] Filed: Feb. 17, 1998

[30]     Foreign Application Priority Data

Feb. 18, 1997 [DE] Germany ............... 197 06 145

[51] Int. Cl.⁷ ..................................... F28F 13/06
[52] U.S. Cl. ................. 210/175; 210/194; 165/108; 165/109.1; 165/132; 165/287; 4/545; 261/DIG. 29
[58] Field of Search .................. 4/545; 165/108, 165/109.1, 132, 287; 210/175, 194; 261/DIG. 29

[56]     References Cited

U.S. PATENT DOCUMENTS

| | | | |
|---|---|---|---|
| 4,664,793 | 5/1987 | Murakami et al. | 210/181 |
| 4,859,345 | 8/1989 | Inagaki | 210/764 |
| 5,100,563 | 3/1992 | Suzuki | 210/747 |
| 5,158,689 | 10/1992 | Ishii et al. | 210/762 |
| 5,208,923 | 5/1993 | Stiver | 4/493 |

*Primary Examiner*—Duane Smith
*Assistant Examiner*—Betsey J. Morrison

[57]     ABSTRACT

Installation for the sterilization of a body of water wherein the water is conveyed through a heat exchanger to a heat source, where it is heated up to the sterilization temperature. This stream of hot water transfers its heat to the incoming stream of water, leaving the heat exchanger at a temperature that is only slightly higher than that of the incoming water.

10 Claims, 3 Drawing Sheets

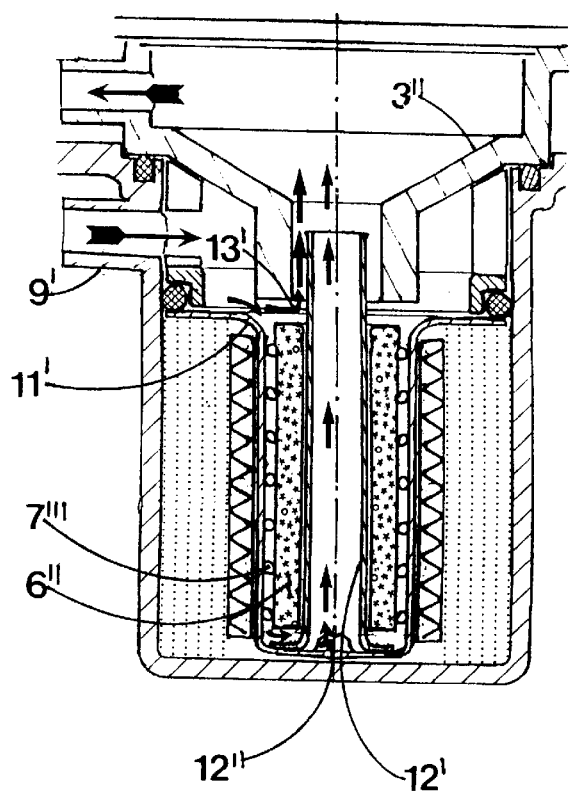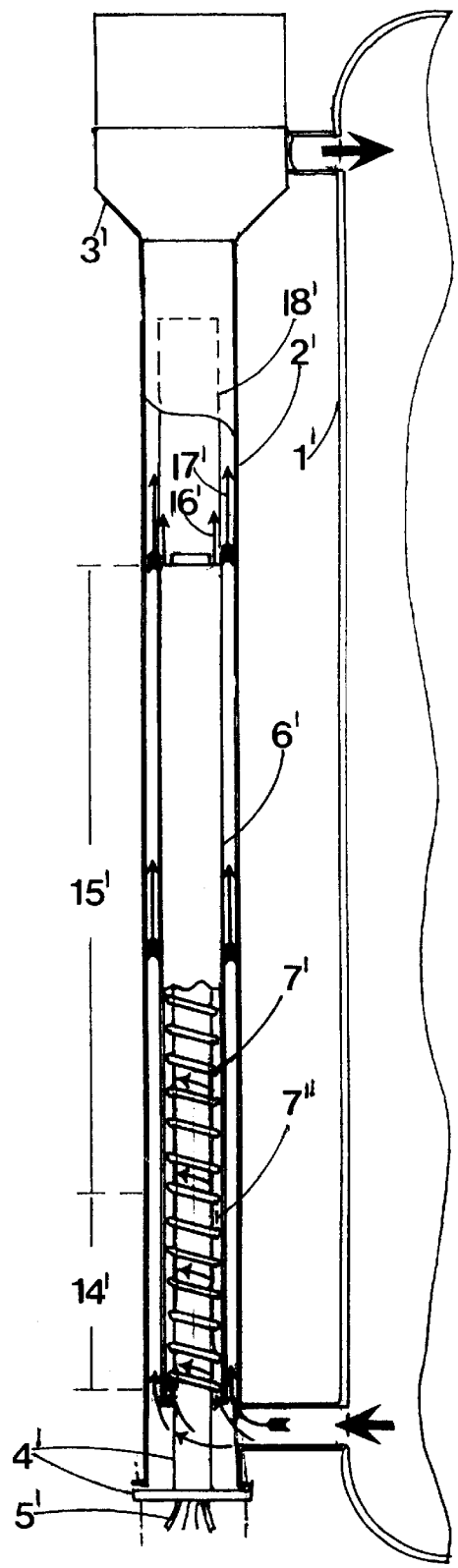

PROCESS AND DEVICE TO STERILIZE A STREAM OF WATER

FIELD OF THE INVENTION

The invention refers to a process and device for the sterilization of a stream of water. The device comprises a heating element that heats water to a temperature at which microbes are killed. If the process is applied to a tub, an electrically driven pump is necessary.

BACKGROUND OF THE INVENTION

In constantly heated tubs with water circulation by a pump pathogenic germs, especially Legionellae, tend to multiply. To eliminate the danger of infection, chlorine or bromine compounds are added at regular intervals. There are also methods known which describe the injection of ozone into the water. All these methods are accompanied by odors. In addition there is a danger for the bath user in case the water treatment is not done regularly. Legionellae are also known to infect drinking water, where they can be combatted by addition of chlorine.

SUMMARY OF THE INVENTION

The invention avoids these drawbacks. According to the invention the heat flux which is necessary to keep the temperature of the bath at the desired value will not be applied to the total water circulated, but only to a fraction, forming a by-pass, which is so small that the heat flux heats it to a temperature which lies above the temperature killing the microbes. It has been shown that the microbes in the by-pass stream have to be exposed to this temperature for a certain time. Therefore, the by-pass throughput has to stay in contact with the heat-supplying surface of the heating element for a certain time before it is re-admixed to the unheated main stream. Each part of the water in the tub will sooner or later be conveyed through the by-pass. If the rate of killing the microbes exceeds the multiplication rate of the microbes in the tub, finally this method will kill all microbes, thus eliminating the danger of infection.

The invention will be described with the help of the following figures.

FIG. 6 shows a sterilizer in the form of a tube.

FIG. 7 shows a sterilizer with a ring-shaped heating element.

Figure 1:
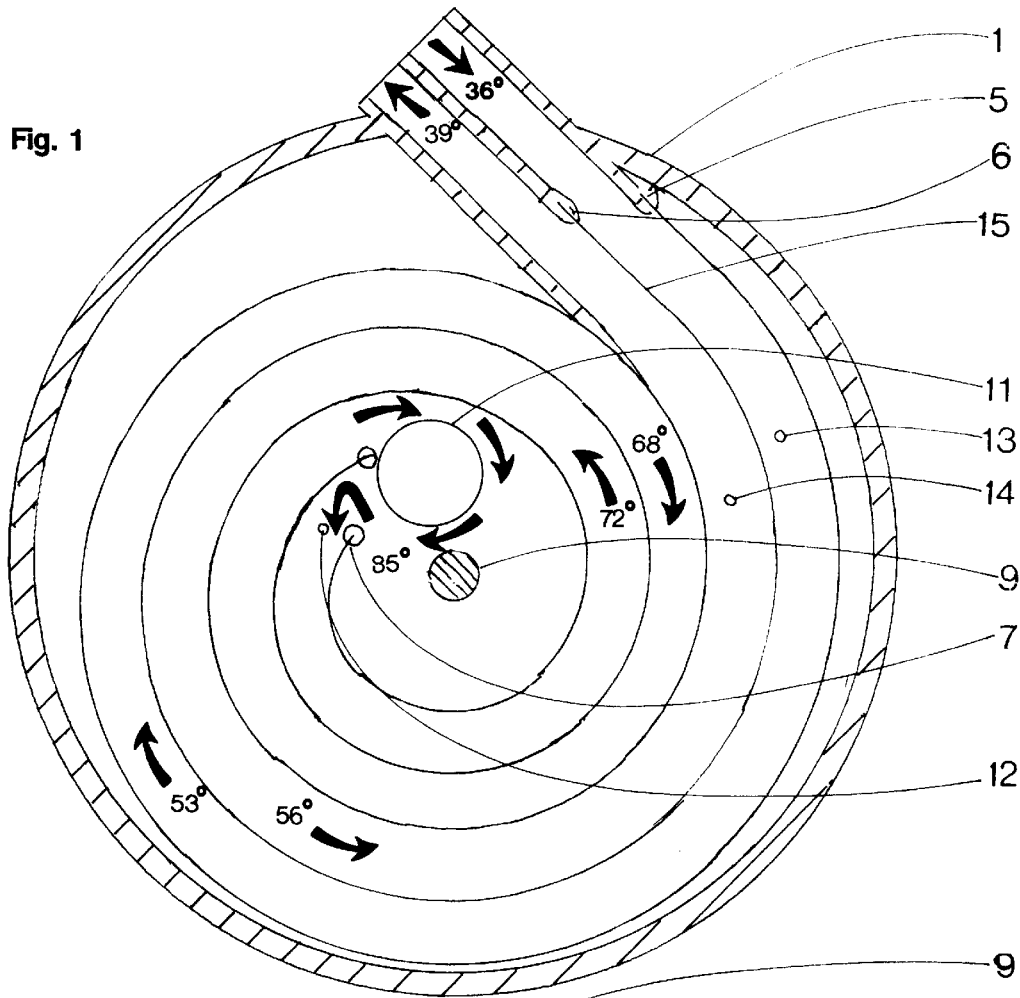
FIGS. 1 and 2 show a counter-flow heat exchanger with spirally extending heat-transferring walls.
Figure 2:
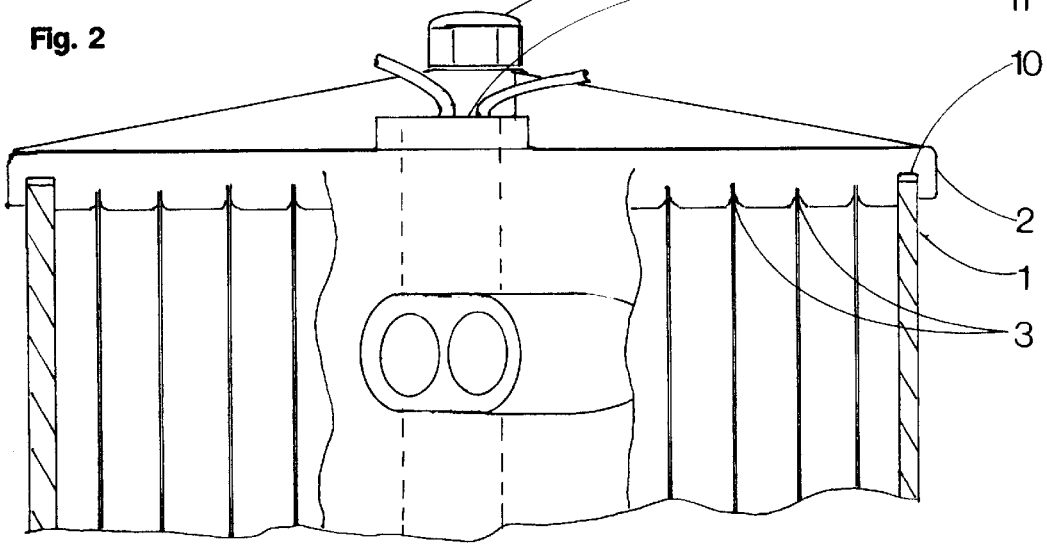

The counter-flow heat exchanger in FIGS. 1 and 2 comprises spirally running heat transferring walls 15, a heating element 11, and a housing consisting of a ring shaped outer wall 1 and two endplates 2. The endplates have spiral grooves 3, into which strips 15, preferably made from plastic, are inserted. The ends of the strips 15 extend into slots 5, 6, 7 and 12, arranged parallel to the axis of the housing formed by the wall 1 and the endplates 2. A screw 9 presses the endplates against the wall 1 with interposed O-rings 10. In the inside, close to the center a heating element 11 is placed that heats the incoming water to the sterilization temperature. From there the heated up water leaves the container with the outer wall 1 and endplates 2 through channel 14 whereby the outgoing stream transfers its heat through the wall 15 to the incoming stream in channel 13. If the counter-flow heat exchanger is part of a closed circuit with a circulation pump, this reduces the heat requirement to an amount necessary to keep the bath at a constant temperature. When the rate of extinction of microbes exceed their production rate, this sterilization method gradually leads to a germ-free bath.

The sterilization of drinking water requires an immediate germ-free result. In addition, the heating of the water is not desirable, the temperature of the sterilized water has to be as low as possible. A design for the drinking water sterilization therefore requires a very large surface of the heat exchange walls 15, whereby the pitch of the spiral becomes very small. In addition the channels 13 and 14 have to be completely sealed from each other within the grooves, which is not necessary for the bath sterilization.

Figure 3:
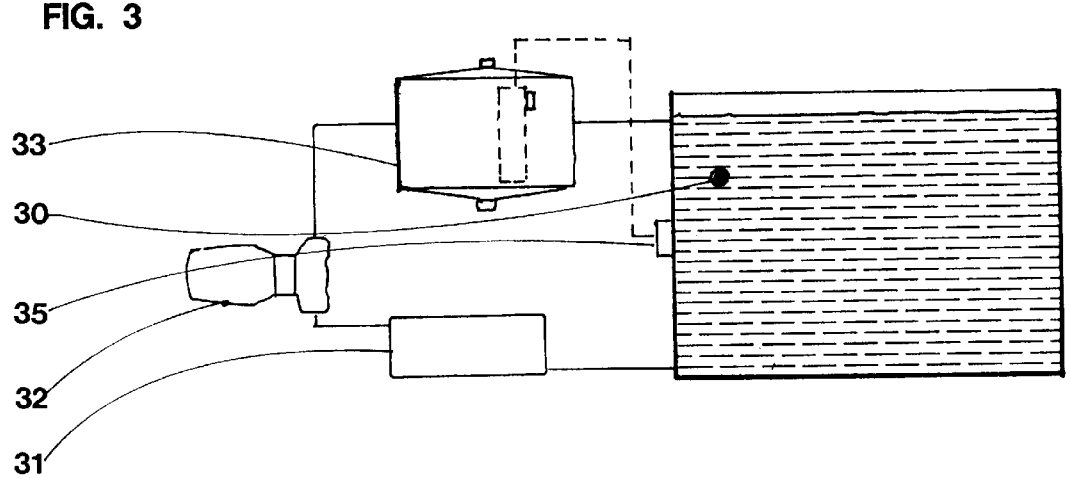
FIG. 3 shows the diagram for the bath sterilization.

FIG. 3 shows the installation for a bath 30 which communicates via a filter 31 with the circulation pump 32. This circulation pump 32 conveys water through the counter flow heat exchanger 33, where it is heated to a temperature which kills the microbes. Thereafter the water transfers its heat to the stream entering the heat exchanger. A thermo switch 35 interrupts the circuit as soon as the bath temperature is reached.

Figure 4:
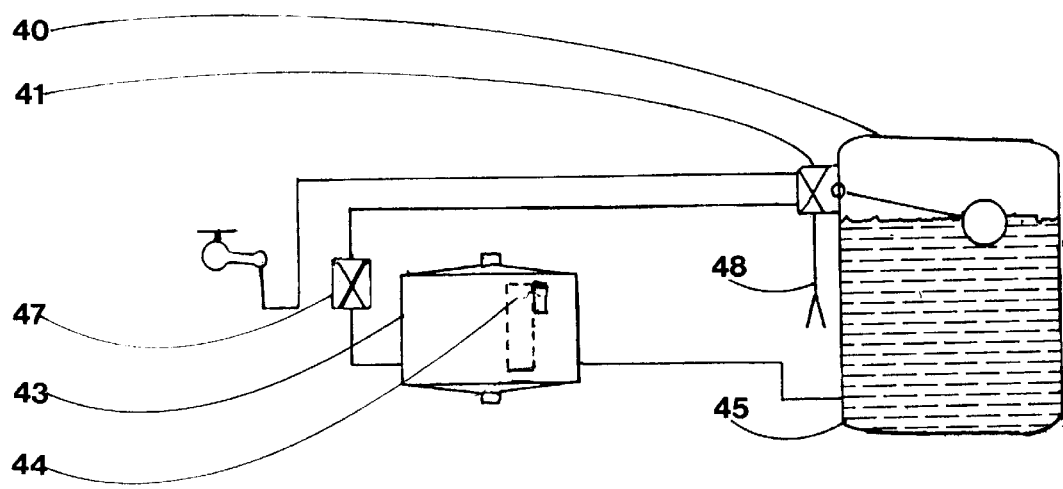
FIG. 4 shows the diagram for drinking water sterilization.

FIG. 4 shows an installation to sterilize drinking water. Via a float valve 41 in a storage tank 40 water from the main reaches the counter flow heat exchanger 43 where the heat from the sterilized water is transferred to the incoming stream and additional heat is applied by the heating element 44 until the sterilization temperature has been reached. Thereafter, the sterilized, cooled down water is stored within the storage tank 40, from where the cold water distribution line is supplied. The float valve 41 doses the influx of fresh water as soon as the storage tank 45 is filled. The valve 47 opens when the sterilization temperature in the area of the heating element has been reached.

Figure 5:
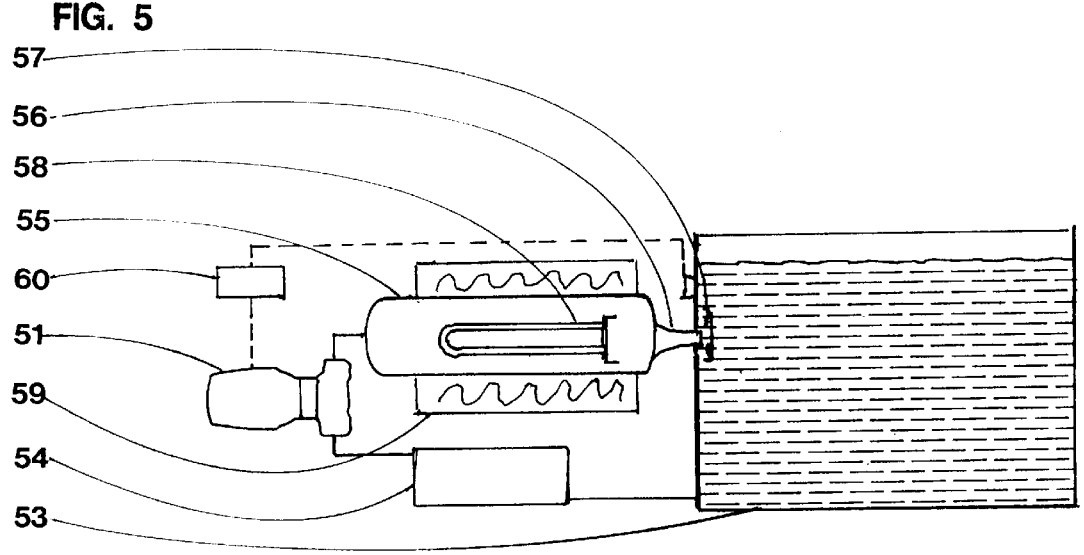
FIG. 5 shows a pulsating version in schematic presentation.

FIG. 5 shows in schematic presentation a pulsating device. The circulation pump 51 sucks the stream of water to be heated through a tube from the lower area of the bath tub 53, preferably through a filter 54, and conveys the water into a vessel 55 that is connected to the outlet nozzle 56. Vessel 55 contains a resistance heater 58, and is surrounded by an insulating wall 59. A switch box 60, switches pump 51 periodically on and off, and at each on-period it conveys an amount of water which equals the volume of the vessel 55. Thereafter, the pump 51 remains inactive until the content of water within the vessel 55 has reached a temperature that is high enough to kill pathogenic microbes. At this point, the switch box 60 turns off the resistance heater 58, and activates the pump that pushes the sterilized content of vessel 55 into the bathtub 53. The outlet nozzle 56 together with the admixing device 57 causes a mixing of the hot water with the water in the bathtub. Then pump 51 is switched off. After an interval, that is shorter the larger the heat requirement for the bathtub 53 is, the cycle starts anew. This device also leads gradually to a sterilization, if the number of microbes destroyed exceeds their proliferation rate.

In FIG. 6 a tub 1' is connected via a pipe 2' with the pump 3'. Pipe 2' contains a rod-like resistance heater 4' with leads 5' on one end. This heater 4' forms together with a plastic separation tube 6' an annular channel 7" through which a helically wound wire 7' runs, guiding the throughput along the helix. When the pump 3' is switched on, there is a pressure difference between the two ends of the annular channel 7" so that there is a flow of water 16'. The width of the annular channel 7" and the pitch of the wire helix 7' are chosen such that the partial flow traveling through the annular channel 7" is heated up by the resistance heater 4' in the area 14' to a predetermined temperature, and that this water stays within the area 15' at this temperature for a predetermined time.

Thereafter, the partial flow 16' exits the annular channel 7" and will be mixed with the parallel flow 17'. The predetermined temperature and the duration of dwell at this temperature is dependent on the kind of microbes, whereby a general rule is that the higher the temperature the shorter the duration of dwell. The temperature of the flow 17' admixed with the flow 16' is chosen such, that it compensates the heat loss of the tub 1', which is normally covered by a lid, if it is not in use. The resistance heater 4' has a flange and can be removed by unscrewing. The helical wire 7' can also be removed for cleaning purposes. The energy density in the heating area 14' of the annular channel 7" should be high, while within the dwelling area 15' only a heat flux is necessary that keeps the water temperature at a value that kills the microbes. It is advantageous if a further area 18' of a length 16' has extremely high heat density that serves for the initial heating of a fresh bathtub filling.

FIG. 7 shows a compact version. The water enters through inlet port 9', the largest part flowing according to arrow 13' into the suction area 3" of the pump (not shown) and to a small part through the annular channel between the container 11' and the insulated pipe section 6". Also in this case the path of the water through the annular channel is determined by the helix 7'". As soon as all microbes are killed, the water heated within the annular channel exits through holes 12" into the inner pipe 12' and from there it is conveyed into the housing 3" of the pump.

The sterilization devices according to the invention can also be arranged between the pressure side of the pump and the bath 1'.

What is claimed is:

1. Counter flow heat exchanger with a heating element to sterilize a flow of water by heat with an inlet opening and an outlet opening, comprising a ring-shaped outer wall (1) and two endplates (2) with a heating element (11) positioned near the center of the ring-shaped outer wall (1), having a first heat transferring separaton-wall (15) that forms with a second heat transferring separation-wall an elongated inwardly spiraling first channel (13) which starts at the inlet opening and ends close to the heating element (11) where the flow of water absorbs its heat, and with a second outwardly spiraling channel (14) that starts close to the heating element (11) and ends at the outlet opening, whereby the heat transferring separation-wall (15) conducts heat from the second channel (14) to the first channel (13) thus preheating the newly entering flow of water.

2. Installation according to claim 1, characterized in that the endplates (2) have spiral grooves (3) which guide the heat transferring separation walls (15).

3. Installation according to claim 2, characterized in that the heat transferring separation walls (15) consist of hydrolyze resistant organic film.

4. Installation according to claim 2, characterized in that the end portions of the heat transferring separation walls ending close to the periphery extend into grooves (5, 6) running parallel to the axis of the counter flow heat exchanger.

5. Installation according to claim 1, characterized in that the endplates (2) are pressed against the ring shaped wall (1) by a rod (9) which extends through the center of the endplates (2).

6. Installation according to claim 1 with a storage tank, characterized in that the counter—flow heat exchanger (43) is connected to a fresh water supply line (48) via a float valve (41) whose float is situated within the storage tank (45).

7. Installation according to claim 1, characterized in that a valve (47) within a loop connecting a tank (40) with the counter-flow heat exchanger (43) opens after a temperature sensor (44) signals that the sterilization temperature has been reached.

8. Installation according to claim 1, characterized in that an annular channel (7") between a heating element (4') and a separation tube (6') forms together with an outer pipe (2') an outer annular channel through which a major part of the water flow (17') is conveyed.

9. Installation according to claim 8, characterized in that a cylindrical heating element (4') reaching into the separation tube (6') forms together with said tube (6') an annular channel (7") through which a smaller part of the water flow (16') is conveyed.

10. Installation according to claim 9, characterized in that a helically wound wire (7') extends through the annular channel (7") whose windings cause the water to flow between two neighboring windings (7').

* * * * *